United States Patent
Zhou et al.

(10) Patent No.: US 11,168,256 B2
(45) Date of Patent: Nov. 9, 2021

(54) LIQUID CRYSTAL MIXTURE AND TEMPERATURE-RESPONSIVE INFRARED REFLECTION DEVICE

(71) Applicants: South China Normal University, Guangzhou (CN); Shenzhen Guohua Optoelectronics Co., Ltd., Shenzhen (CN); Academy of Shenzhen Guohua Optoelectronics, Shenzhen (CN)

(72) Inventors: Guofu Zhou, Guangzhou (CN); Xiaowen Hu, Guangzhou (CN); Wei Zhao, Guangzhou (CN); Weijie Zeng, Guangzhou (CN); Chun Ju, Guangzhou (CN); Lingling Shui, Guangzhou (CN)

(73) Assignees: South China Normal University, Guangzhou (CN); Shenzhen Guohua Optoelectronics Co., Ltd., Shenzhen (CN); Academy of Shenzhen Guohua Optoelectronics, Shenzhen (CN)

( * ) Notice: Subject to any disclaimer, the term of this patent is extended or adjusted under 35 U.S.C. 154(b) by 73 days.

(21) Appl. No.: 16/604,371

(22) PCT Filed: Oct. 10, 2018

(86) PCT No.: PCT/CN2018/109640
§ 371 (c)(1),
(2) Date: Oct. 10, 2019

(87) PCT Pub. No.: WO2019/076220
PCT Pub. Date: Apr. 25, 2019

(65) Prior Publication Data
US 2020/0123445 A1    Apr. 23, 2020

(30) Foreign Application Priority Data
Oct. 17, 2017    (CN) .......................... 201710963567.2

(51) Int. Cl.
*C09K 19/40* (2006.01)
*C09K 19/58* (2006.01)
(Continued)

(52) U.S. Cl.
CPC .............. *C09K 19/40* (2013.01); *C09K 19/52* (2013.01); *C09K 19/586* (2013.01); *G02F 1/132* (2013.01); *C07C 53/126* (2013.01)

(58) Field of Classification Search
CPC ...... C09K 19/40; C09K 19/402; C09K 19/52; C09K 19/54; C09K 19/586; G02F 1/132
See application file for complete search history.

(56) References Cited

U.S. PATENT DOCUMENTS

2006/0088667 A1*  4/2006  Iftime ................ G02F 1/13476
                                                   428/1.1
2014/0320776 A1* 10/2014  Taheri .................. G02F 1/0045
                                                   349/16

FOREIGN PATENT DOCUMENTS

WO       2016048016 A1    3/2016

OTHER PUBLICATIONS

Melnik et al., "Microscopic Textures of Micellar Cholesteric Liquid Crystals", 1987, Molecular Crystals and Liquid Crystals, vol. 145, 95-110. (Year: 1987).*

(Continued)

*Primary Examiner* — Chanceity N Robinson
*Assistant Examiner* — Anna Malloy
(74) *Attorney, Agent, or Firm* — Christopher & Weisberg, P.A.

(57) ABSTRACT

A liquid crystal mixture and a temperature-responsive infrared reflection device made by using the liquid crystal mixture containing potassium laurate. Infrared light can pass through the device within a non-working temperature range, and a chiral dopant enables potassium laurate to form a (Continued)

cholesteric phase within a working temperature range. The birefringence value of the potassium laurate gradually increases with the increase of temperature between 12.5° C. and 26° C., so that the infrared reflection bandwidth of the device constantly increases. The birefringence value of the potassium laurate gradually decreases with the increase of temperature between 26° C. and 54.5° C., so that the infrared reflection bandwidth of the device constantly decreases. The infrared reflection bandwidth of the infrared reflection device can vary with temperature by adjusting the proportions of the ingredients of the liquid crystal mixture containing potassium laurate.

5 Claims, 2 Drawing Sheets

(51) Int. Cl.
*C09K 19/52* (2006.01)
*G02F 1/13* (2006.01)
*C07C 53/126* (2006.01)

(56) References Cited

OTHER PUBLICATIONS

Internation Search Report and Written Opinion dated Jan. 9, 2019, for corresponding International Application No. PCT/CN2018/109640; International filing date Oct. 10, 2018; consisting of 8—pages.
Braga et al., "Reentrant isotropic-calamitic nematic phase transition in potassium laurate-decanol-D20 mixtures," The European Physical Journal E, vol. 24, 2007, pp. 247-250; consisting of 5—pages.
Licinio et al., "Pretransitional scaling close to a double critical point in a potassium laurate, 1-decanol, and heavy water lyotropic liquid crystal," Physical Review E, vol. 65, 2002, pp. 031714-1-031714-4; consisting of 5—pages.
Kimura et al., "Reentrant isotropic—discotic nematic lyotropic phase transition: a refractive index study," Liquid Crystals, vol. 31, No. 00, pp. 1-4; consisting of 5—pages.
Santoro et al., "Temperature dependence of refractive indices near uniaxial-biaxial nematic phase transition," Physical Letters A, vol. 353, 2006, pp. 512-515; consisting of 5—pages.

\* cited by examiner

LIQUID CRYSTAL MIXTURE AND TEMPERATURE-RESPONSIVE INFRARED REFLECTION DEVICE

CROSS-REFERENCE TO RELATED APPLICATIONS

This application is a Submission under 35 U.S.C. § 371 for U.S. National Stage Patent Application of, and claims priority to, International Application Number PCT/CN2018/109640 entitled LIQUID CRYSTAL MIXTURE AND TEMPERATURE-RESPONSIVE INFRARED REFLECTION DEVICE, filed Oct. 10, 2018, which is related to and claims priority to Chinese Patent Number 201710963567.2, filed Oct. 17, 2017, the entirety of all of which are incorporated herein by reference.

TECHNICAL FIELD

The present disclosure relates to the technical field of optical devices, and particularly to a liquid crystal mixture and a temperature-responsive infrared reflection device.

BACKGROUND

In order to achieve the transmission and reflection of infrared light in sunlight, it is generally to coat a film on glass, so that, in the infrared light, light within a certain range of wavelengths can be reflected or transmitted by a glass window. Coating a film on glass refers to coat the surface of the glass with one or more layers of metal, alloy or metal compound films to change the optical properties of the glass, so as to reflect or transmit the light within a certain range of wavelengths. However, the optical properties of the coated glass, after the molding thereof, cannot change with the variation of environment. As the diversity of climate, the coated glass cannot meet people's needs.

SUMMARY

One technical problem to be solved by the present disclosure is to provide a liquid crystal mixture and a temperature-responsive infrared reflection device. It can meet people's needs with the variation of environment, and can be applied in many fields such as households and buildings.

The technical solutions adopted by the present disclosure are as follows.

The present disclosure provides a liquid crystal mixture which may include potassium laurate, heavy water, organic alcohol, and a chiral dopant.

Preferably, the organic alcohol may be one of n-decanol, iso-decanol and n-octanol.

Preferably, the chiral dopant may be S1011 or R1011.

Preferably, the liquid crystal mixture may include 24.03 to 28.9 parts by weight of potassium laurate, 5.7 to 7.3 parts by weight of heavy water, 59.8 to 69.2 parts by weight of organic alcohol, and 2.71 to 2.83 parts by weight of chiral dopant.

The present disclosure also provides a temperature-responsive infrared reflection device, which may include the above liquid crystal mixture.

Preferably, the temperature-responsive infrared reflection device can reflect infrared light at 12.5° C. to 54.5° C.

The present disclosure has the following advantages.

The present disclosure provides a liquid crystal mixture and a temperature-responsive infrared reflection device. The liquid crystal mixture can be obtained by mixing potassium laurate, heavy water, organic alcohol and chiral dopant. The liquid crystal mixture can reflect infrared light in a certain range of wavelengths at 12.5° C. to 54.5° C. From 12.5° C. to 26° C., the birefringence value of potassium laurate can increase with the increase of temperature, such that the infrared reflection bandwidth of the infrared reflection device made by using such liquid crystal mixture can also constantly increase and reach the peak at 26° C. From 26° C. to 54.5° C., the birefringence value of the potassium laurate can decrease with the increase of temperature, such that the infrared reflection bandwidth of the infrared reflection device made by using such liquid crystal mixture can gradually decrease. The infrared reflection bandwidth of the infrared reflection device can vary with temperature by adjusting the proportions of the ingredients of the liquid crystal mixture containing potassium laurate. Therefore, the temperature-responsive infrared reflection device of the present disclosure can satisfy the demands of people which vary with the environment, and can be applied in many fields such as households and buildings.

DETAILED DESCRIPTION

Hereinafter, with reference to the embodiments and drawings, the conception, specific structures and technical effects of the present disclosure are to be clearly and completely described to fully understand the objectives, features and effects of the present disclosure. It is apparent that the following embodiments are only a part of the embodiments of the present disclosure, and are not all of the embodiments. Based on the embodiments of the present disclosure, other embodiments, which can be obtained by those skilled in the art without creative efforts, belong to the scope of protection of the present disclosure.

Example 1

A liquid crystal mixture is obtained by mixing 25 parts by weight of potassium laurate, 6.8 parts by weight of heavy water, 65.45 parts by weight of n-decanol, and 2.75 parts by weight of chiral dopant S 1011 well.

The potassium laurate has a structural formula as shown by

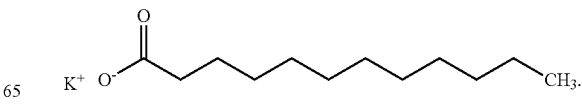

The chiral dopants S 1011 and R 1011 used herein have similar structural formulae as shown by

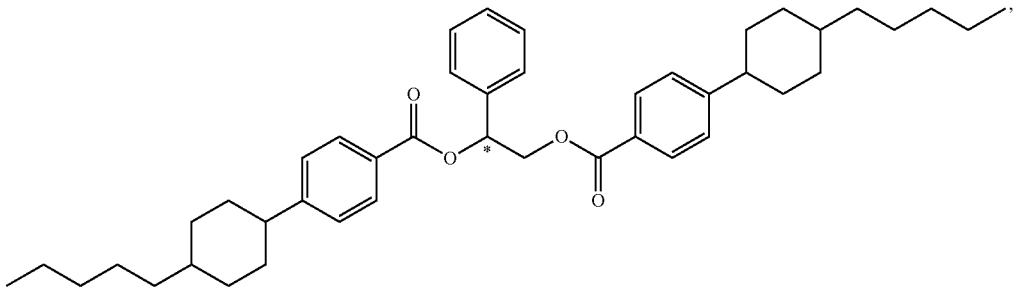 [SMILES: CCCCCC1CCC(c2ccc(C(=O)OCC(OC(=O)c3ccc(C4CCC(CCCCC)CC4)cc3)c3ccccc3)cc2)CC1]

but opposite chirality.

Example 2

A liquid crystal mixture is obtained by mixing 25 parts by weight of potassium laura(e, 6.5 parts by weight of heavy water, 65.73 parts by weight of n-octanol, and 2.75 parts by weight of chiral dopan(well.

Example 3

A liquid crystal mixture is obtained by mixing 27.52 parts by weight of potassium laurate, 6.89 parts by weight or heavy water, 62.8 parts by weight or iso-decanol, and 2.79 parts by weight of chiral dopant R1011 well.

Example 4

Figure 1:
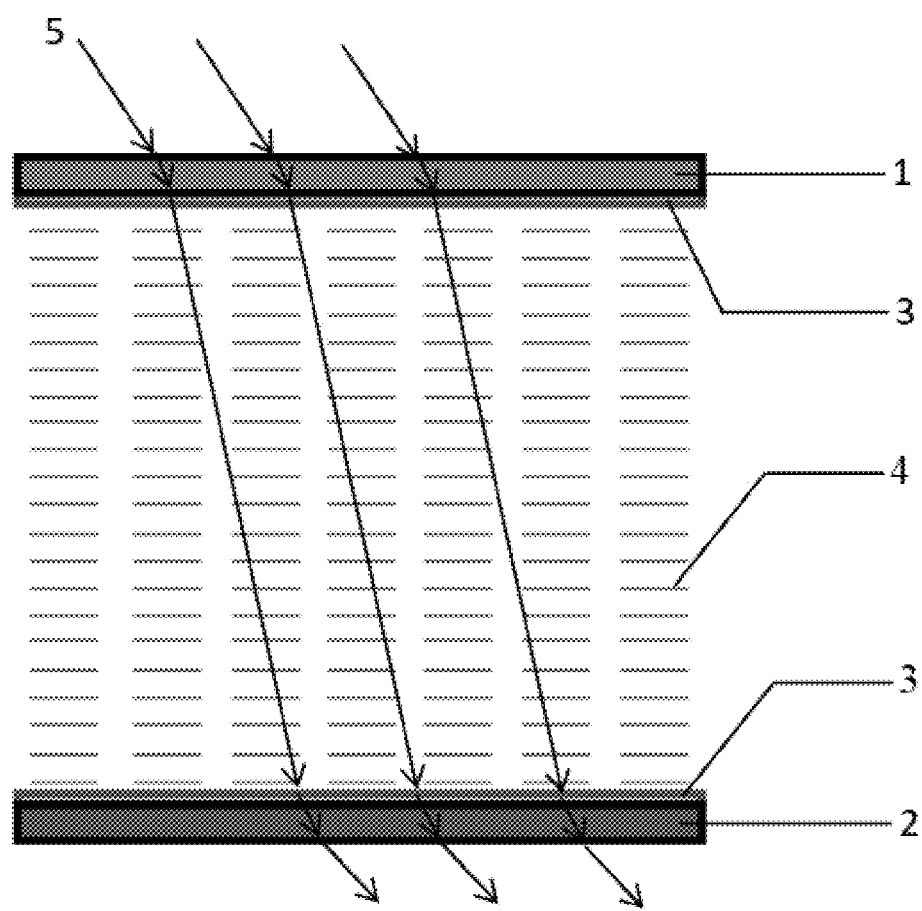
FIG. 1 is a partial cross-sectional schematic diagram of a temperature-responsive infrared reflection device at a non-working temperature (outside the range of 12.5° C. to 54.5° C.)

This example provides a temperature-responsive infrared reflection device, as shown in FIG. 1.

The temperature-responsive infrared reflection device comprises a first light-transmitting substrate 1 and a second light-transmitting substrate 2 which are arranged relatively. The opposite surfaces of the first light-transmitting substrate 1 and the second light-transmitting substrate 2 are spin-coated with parallel alignment layers 3, and are arranged through rubbing alignment. The liquid crystal mixture, which may be the mixture of Example 1, fills between the first light-transmitting substrate 1 and the second light-transmitting substrate.

When the temperature-responsive infrared reflection device of this example is at non-working temperature (outside the range of 12.5° C. to 54.5° C.), potassium laurate 4 cannot form a cholesteric phase with the chiral dopant of the liquid crystal mixture, and would be in isotropic status. Thus, infrared light 5 can pass through the device without affecting the transmission of visible light. In this example, the liquid crystal mixture of Example 1 is heated to convert potassium laurate into isotropic status, and then injected into the device, during the preparation of the temperature-responsive infrared reflection device. It would facilitate the filling by heating potassium laurate to reduce the viscosity thereof.

Figure 2:
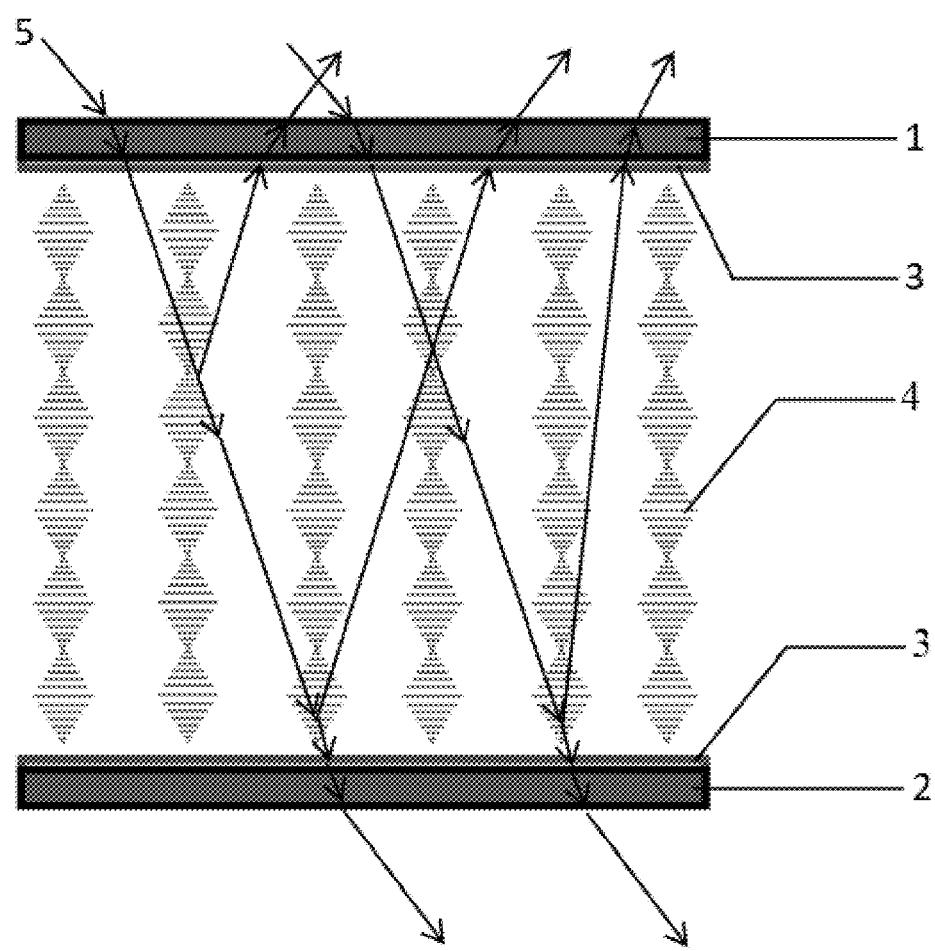
FIG. 2 is a partial cross-sectional schematic diagram of a temperature-responsive infrared reflection device at a working temperature (12.5° C. to 54.5° C.).

Referring to FIG. 2, when the temperature-responsive infrared reflection device of this example is at working temperature (12.5° C. to 54.5° C.), potassium laurate 4 can form a cholesteric phase of a spiral structure with the chiral dopant of the liquid crystal mixture, to reflect infrared light 5 within a certain range of wavelengths. From 12.5° C. to 26° C., the birefringence value (Δn) of potassium laurate 4 increases with the increase of temperature and reach the peak at 26° C. The infrared reflection bandwidth of the infrared reflection device, which is made by using the liquid crystal mixture of Embodiment 1, also constantly increases and reach the peak at 26° C. From 26° C. to 54.5° C., the birefringence value (Δn) of potassium laurate 4 decreases with the increase of temperature. The infrared reflection bandwidth of the infrared reflection device, which is made by using the liquid crystal mixture of Example 1, gradually decreases. Therefore, from 12.5° C. to 54.5° C., the infrared reflection bandwidth of the infrared reflection device, which is made by using the liquid crystal mixture, can vary with external temperature.

Example 5

A liquid crystal mixture is obtained by mixing 28 parts by weight of potassium laurate, 7.3 parts by weight of heavy water, 61.9 parts by weight of n-decanol, and 2.8 parts by weight of chiral dopant R1011 well.

Example 6

A liquid crystal mixture is obtained by mixing 26 parts by weight of potassium laurate, 5.9 parts by weight of heavy water, 65.34 parts by weight of iso-decanol, and 2.76 parts by weight of chiral dopant S1011 well.

What is claimed is:

1. A liquid crystal mixture, comprising:

24.03 to 28.9 parts by weight of potassium laurate;

5.7 to 7.3 parts by weight of heavy water;

59.8 to 69.2 parts by weight of organic alcohol; and 2.71 to 2.83 parts by weight of chiral dopant.

2. The liquid crystal mixture of claim 1, wherein the organic alcohol is one selected from the group consisting of n-decanol, iso-decanol and n-octanol.

3. The liquid crystal mixture of claim 1, wherein the chiral dopant has the structural formula

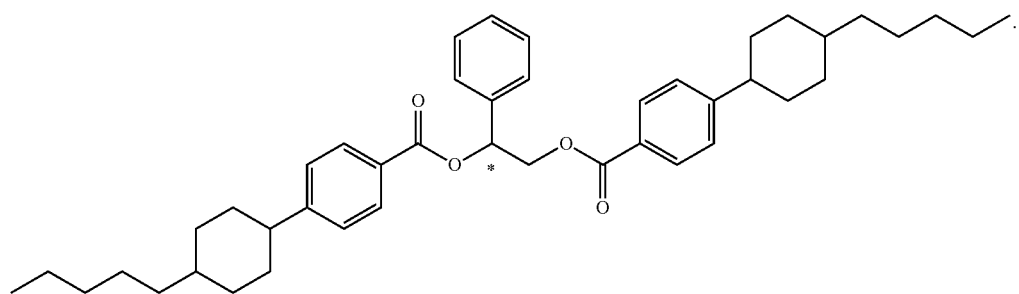 [SMILES: CCCCCC1CCC(c2ccc(C(=O)OCC(OC(=O)c3ccc(C4CCC(CCCCC)CC4)cc3)c3ccccc3)cc2)CC1]
4. A temperature-responsive infrared reflection device, comprising the liquid crystal mixture of claim 1.
5. The temperature-responsive infrared reflection device of claim 4, wherein the temperature-responsive infrared reflection device is capable of performing infrared reflection at 12.5° C. to 54.5° C.
* * * * *